United States Patent [19]

Kepp et al.

[11] Patent Number: 5,247,927
[45] Date of Patent: Sep. 28, 1993

[54] TRACHEAL TUBE WITH PERMEATION-STABLE BLOCKING CUFF

[75] Inventors: Werner Kepp, Waiblingen; Klaus Schmitt, Remshalden, both of Fed. Rep. of Germany

[73] Assignee: Willy Rush AG, Fed. Rep. of Germany

[21] Appl. No.: 880,077

[22] Filed: May 7, 1992

[30] Foreign Application Priority Data

May 11, 1991 [DE] Fed. Rep. of Germany ....... 4115497

[51] Int. Cl.$^5$ .............................................. A61M 16/00
[52] U.S. Cl. ............................. 128/207.15; 128/207.14
[58] Field of Search ...................... 128/207.14, 207.15

[56] References Cited

U.S. PATENT DOCUMENTS 3,503,399  3/1970  Ettman et al. ...................... 604/100
4,335,723  6/1982  Patel ..................................... 604/97

FOREIGN PATENT DOCUMENTS 0229862   1/1986  European Pat. Off. .
204500   12/1986  European Pat. Off. .
3921524   6/1989  Fed. Rep. of Germany .
8915538   7/1989  Fed. Rep. of Germany .
9100090   1/1991  Fed. Rep. of Germany .
2008140   5/1979  United Kingdom .
8401294   4/1984  World Int. Prop. O. .

OTHER PUBLICATIONS

Kunststoff-Lexikon, Carl-Hanser-Verlag, 7. Auflage (1981), Seite 167, rechts unten bis Seite 168, Absatz 1.

Primary Examiner—Edgar S. Burr
Assistant Examiner—Aaron J. Lewis
Attorney, Agent, or Firm—Walter A. Hackler

[57] ABSTRACT

At a tube shaft 2 a tracheal tube 1 has a blocking cuff 4 made of a material which has the structure of a synthetic caoutchouc mixed polymer. A blocking cuff 4 designed in such a way is not permeable to anesthesia gas and may be manufactured to have one layer. Preferably the blocking cuff 4 is made of butadiene acrylnitrile mixed polymer.

3 Claims, 1 Drawing Sheet

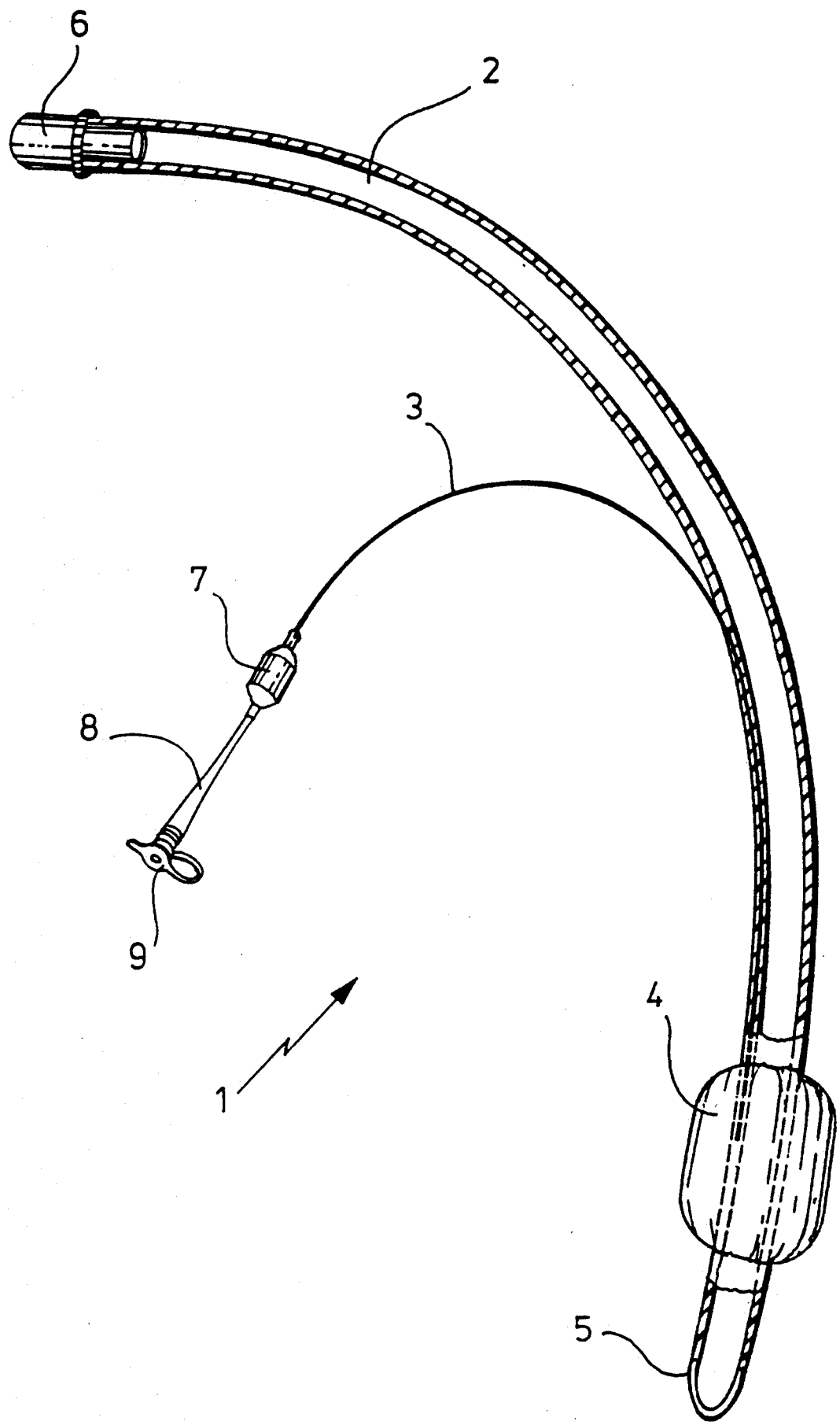

TRACHEAL TUBE WITH PERMEATION-STABLE BLOCKING CUFF

BACKGROUND OF THE INVENTION

The invention relates to a tracheal tube with a permeation-stable blocking cuff arranged at a shaft.

Such a tracheal tube has been known from DE 39 21 524 A1.

Such tracheal tubes are preferably used with endotracheal anesthesia. After intubation the blocking cuff is in situ filled with air. Then the blocking cuff locks the gap between trachea and the respiration hose in such a way that the inspiration mixture cannot escape anymore and flows into the lungs. Experiments have shown that the pressure of the blocking cuff may increase greatly during intubation anesthesia with certain anesthesia gases, the cause being that during intubation anesthesia the anesthesia gas diffuses into the blocking cuff. This results in a volume change of the gas in the blocking cuff and it presses against the trachea's mucous membrane with an increased pressure. On the one hand, the increase in pressure in the blocking cuff may result in damages of the tracheal wall and, on the other, the blocking cuff may deform in addition plastically in the case of pressures which are too great. If the plastical deformation occurs on the side of the blocking cuff which faces the tube's tip, this may even result in a partial or total lumen displacement of the tube's shaft in the area of the tube's tip.

The changes in volume and thus related changes in pressure within the blocking cuff depend on the concentration difference of the anesthesia gas to the blocking cuff, on the acting time of the anesthesia gas on the blocking cuff and the degree of the blocking cuff's permeability to gas, among other things.

The known tracheal tube provides a low-pressure blocking cuff designed in a multi-layer way with a great surface having relatively thin walls. The volume of the cuff is pre-determined and the blocking cuff can develop in situ without a considerable increase in pressure. The blocking cuff is not permeable to anesthesia gases because it has at least one material layer, for example a metal foil, which is not permeable to anesthesia gas. The materials used with the known blocking cuff have to be well-adapted to each other such that they lie form-fittingly against each other without that pressure is exerted as well as in the state when pressure is exerted, in order to prevent undesired folds. Moreover, in the transitional areas to the shaft a very careful material joint has to be provided, in order that here preferably diffusion areas are prevented.

SUMMARY OF THE INVENTION

At a tube shaft a tracheal tube has a blocking cuff made of a material which has the structure of a synthetic caoutchouc mixed polymer. A blocking cuff designed in such a way is not permeable to anesthesia gas and may be manufactured to have one layer. Preferably the blocking cuff is made of butadiene acrylnitrile mixed polymer.

Therefore, it is the object of the present invention to develop a tracheal tube of the above mentioned kind in such a way that it is designed with a simple blocking cuff with which during the periods it is usually used no or only a neglectably small amount of anesthesia gas can diffuse from the trachea into the blocking cuff.

According to the present invention this object is solved by the fact that a material having a sufficient layer thickness which has the structure of an elastomeric synthetic caoutchouc mixed polymer is used for the blocking cuff.

The structure design of the material of the blocking cuff according to the present invention is such that for example $N_2O$ molecules cannot penetrate to a considerable extend. By using such a blocking cuff pressure-induced trauma of the mucous membrane can be excluded. A permanent seal and a one which is gentle to the raucous membrane between the tube's shaft and trachea is achieved.

Suitably cross-linked elastomers of nitrile caoutchouc or chloroprenes, neoprenes, chlorinated caoutchoucs are also especially thermo-stable apart from a good permeability. Therefore, tubes having a blocking cuff according to the present invention can be re-sterilized especially well. According to the present invention synthetic mixed polymers which are resistant to organic solvents to a considerable extend are used for the manufacture of the blocking cuff. A swelling up of the mixed polymers or that they start to dissolve is prevented due to the contact with organic solvents.

Tracheal tubas having the blocking cuff according to the present invention can be manufacutured with lower costs, because an additional layer design or additional components are not needed.

In an preferred embodiment of the present invention the blocking cuff has an one-layer design. This has the advantage that it can be manufactured in a very thin wall thickness and the formation of folds which is disadvantageous in the used is avoided. The material thickness is between 0.1 and 1.15 mm.

In a preferred embodiment of the invention the blocking cuff is formed by a butadiene acrylnitrile mixed polymer.

As it is known, nitrite or chlorinated caoutchouc is highly resistant to organic solvents. Moreover, it is known from application areas in the car industry that these synthetic caoutchoucs are insensitive to oil. Anesthetia gases as halogenated hydrocarbons are greatly lipophilic. As experiments have shown, nitrile caoutchouc is also sufficiently resistant to halogenated hydrocarbons and also thermo-stable to such an extend that tracheal tubes with the blocking cuff according to the present invention can be re-sterilized many times. Nitrile caoutchouc can also be well processed in combination with rubber or latex so that the shaft of a tracheal tube may be made of rubber or latex and/or chlorinated caoutchouc, whereas the blocking cuff is made of nitrile caoutchouc. Yet it goes without saying that also other synthetic caoutchoucs may serve as material for the shaft. The diffusion capacity of nitrile caoutchouc for anesthetia gases is extremely low.

A mixture ratio for the material of the blocking cuff of 30% acrylnitrile and 70% butadiene has proven to be especially good.

Thus the tracheal tube according to the present invention lives up to all extended requirements in anesthesiology. It is gentle to the mucous membrane as high-volume and low-pressure cuff, it offers sufficient security against an excessively strong anesthetia gas diffusion and may be designed as a single-use as well as a multi-use tube.

Further advantages will become apparent from the description and the enclosed drawing. The features mentioned above as well as the ones discussed below may also be used in other embodiments of the invention each individually or in any combination thereof. The mentioned embodiments are not to be taken as a final list, but serve as example.

The invention is shown in the drawing and is explained by a FIGURE. The object shown in the FIGURE shows the blocking cuff according to the present invention partly very schematic. The object is not to be taken as full scale.

DETAILED DESCRIPTION

The FIGURE shows a tracheal tube 1 which has a supply hose 3 at a tube shaft 2. The supply tube 3 is preferably guided in the wall of the tube shaft 2 and communicates with a blocking cuff 4 which is mounted at the tube shaft 2. The blocking cuff 4 is arranged near a tip 5 of the tube shaft 2. The blocking cuff 4 is designed with one layer and in the example it is made of synthetic caoutchouc. The blocking cuff shown in the FIGURE is a high-volume/low-pressure cuff.

At the end of the tube shaft 2 facing the machine a standardized connector 6 in provided via which the hoses of a respirator can be gas-tightly connected with the tracheal tube 1 (standardized intersection). In the area of its free end the supply tube 3 has a control balloon 7 which is followed by an injection attachment 8. The injection attachment 8 can be locked by means of a fastener 9. Via the injection attachment 8, the blocking cuff 4 can be either air-inflated or deflated in a manner not shown in the FIGURE.

The blocking cuff 4 is made of a material non-permeable to anesthesia gas which has the structure design of a butadiene acrylnitrile mixed polymer or chloroprene polymer. The tube's shaft may be made of polyvinylchlorid, polyurethane or rubber, synthetic caoutchouc or latex.

The material thickness of a blocking cuff manufactured of a cross-linked elastomer amounts to 0.1 to 0.15 mm and the mixture ratio for use of a butadiene acrylnitrile mixed polymer may amount to between 25% and 35% acrylnitrile and 65% to 75% butadiene.

What is claimed is:

1. Tracheal tube comprising:
    a hollow shaft; and
    an inflatable blocking cuff disposed about the shaft and including means for preventing permeation of gas therethrough, said means for preventing further including having an elastomeric synthetic caoutchouc mixed polymer structure both gas permeation-stable and thermostable, said blocking cuff consisting essentially of a single layer of butadiene acrylnitrile mixed polymer having an acrylnitrile content of between 25% and 35%.

2. Tracheal tube according to claim 1, wherein the thickness of the blocking cuff is between 0.1 mm and 0.15 mm.

3. Tracheal tube according to claim 2, wherein the single layer of butadiene has a butadiene content of between 65% and 75% and provides resistance against organic solvents.

* * * * *

UNITED STATES PATENT AND TRADEMARK OFFICE
CERTIFICATE OF CORRECTION

PATENT NO. : 5,247,927
DATED      : September 28, 1993
INVENTOR(S): Werner Kepp and Klaus Schmitt It is certified that error appears in the above—identified patent and that said Letters Patent is hereby corrected as shown below:

On the title page, item (73) should read:

-- Assignee:  Willy Rusch AG, Fed. Rep. of Germany --.

Signed and Sealed this

Fifth Day of April, 1994

Attest:

BRUCE LEHMAN

Attesting Officer

Commissioner of Patents and Trademarks